(12) United States Patent
Masciotti et al.

(10) Patent No.: US 11,406,298 B2
(45) Date of Patent: Aug. 9, 2022

(54) METHODS AND SYSTEMS FOR CALCULATING ANALYTE LEVELS

(71) Applicant: Senseonics, Incorporated, Germantown, MD (US)

(72) Inventors: James Masciotti, Germantown, MD (US); Abhi Chavan, Germantown, MD (US); Andrew Dehennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 305 days.

(21) Appl. No.: 16/100,699

(22) Filed: Aug. 10, 2018

(65) Prior Publication Data

US 2019/0046095 A1 Feb. 14, 2019

Related U.S. Application Data

(60) Provisional application No. 62/545,121, filed on Aug. 14, 2017.

(51) Int. Cl.
*A61B 5/145* (2006.01)
*A61B 5/1455* (2006.01)
*A61B 5/1459* (2006.01)
*A61B 5/00* (2006.01)
*A61B 5/07* (2006.01)
*G01N 33/58* (2006.01)

(52) U.S. Cl.
CPC ........ *A61B 5/14556* (2013.01); *A61B 5/0031* (2013.01); *A61B 5/0071* (2013.01); *A61B 5/07* (2013.01); *A61B 5/1459* (2013.01); *A61B 5/14503* (2013.01); *A61B 5/14532* (2013.01); *A61B 2562/0257* (2013.01); *A61B 2562/162* (2013.01); *G01N 33/582* (2013.01)

(58) Field of Classification Search
None
See application file for complete search history.

(56) References Cited

U.S. PATENT DOCUMENTS

| 6,344,360 | B1 | 2/2002 | Colvin et al. |
| 9,414,775 | B2 | 8/2016 | Colvin, Jr. et al. |
| 9,427,182 | B2 | 8/2016 | Emken et al. |
| 2004/0043527 | A1* | 3/2004 | Bradley ................ B82Y 15/00 438/48 |

(Continued)

OTHER PUBLICATIONS

Nacht, Barbara et al., "Integrated catheter system for continuous glucose measurement and simultaneous insulin infusion", Biosensors and Bioelectronics, vol. 64, (2015), pp. 102-110, XP055408960.

*Primary Examiner* — Alex M Valvis
*Assistant Examiner* — Aurelie H Tu
(74) *Attorney, Agent, or Firm* — Rothwell, Figg, Ernst & Manbeck, P.C.

(57) ABSTRACT

Disclosed are systems and methods for detecting analyte levels. These systems and methods may include a sensor configured for at least partial placement in an analyte-containing medium. The sensor may include one or more transducers and one or more diffusion barriers. The diffusion barriers may be arranged to delay diffusion of analyte to one transducer relative to another transducer. This delay may be used for purposes such as calculating and/or compensating for lag between a measured analyte level and a physiological analyte level of interest.

11 Claims, 11 Drawing Sheets

(56) References Cited

U.S. PATENT DOCUMENTS

| | | | |
|---|---|---|---|
| 2009/0084678 A1* | 4/2009 | Joshi | G01N 27/4146 |
| | | | 204/403.14 |
| 2009/0131777 A1 | 5/2009 | Simpson et al. | |
| 2009/0137887 A1 | 5/2009 | Shariati et al. | |
| 2011/0024307 A1 | 2/2011 | Simpson et al. | |
| 2013/0241745 A1 | 9/2013 | Colvin, Jr. et al. | |
| 2013/0244266 A1 | 9/2013 | Reardon et al. | |
| 2013/0303869 A1* | 11/2013 | Rebec | A61B 5/14735 |
| | | | 600/365 |
| 2015/0148627 A1 | 5/2015 | Baets et al. | |
| 2015/0148647 A1* | 5/2015 | Liu | G01N 27/3271 |
| | | | 600/395 |
| 2015/0182115 A1* | 7/2015 | DeHennis | G16H 40/63 |
| | | | 600/316 |
| 2015/0199288 A1* | 7/2015 | DeHennis | H04B 5/0075 |
| | | | 506/39 |

\* cited by examiner

METHODS AND SYSTEMS FOR CALCULATING ANALYTE LEVELS

CROSS-REFERENCE TO RELATED APPLICATION

The present application claims the benefit of priority to U.S. Provisional Application Ser. No. 62/545,121, filed on Aug. 14, 2017, which is incorporated herein by reference in its entirety.

BACKGROUND

Field of Invention

The present invention relates to calculating levels in a first medium using measurements from a second medium. More specifically, aspects of the present invention relate to using estimating the rate of change of the level in the second medium using a measurement of the level in the second medium and one or more diffusion barrier-delayed measurements of the level in the second medium. Even more specifically, aspects of the present invention relate to calculating a blood analyte level using a measurement of an interstitial fluid analyte level and one or more measurements of diffusion barrier-delayed measurements of the interstitial fluid analyte level to instantaneously estimate the rate of change of the interstitial fluid analyte level.

Discussion of the Background

Analyte monitoring systems may be used to monitor analyte levels, such as analyte concentrations. One type of analyte monitoring system is a continuous glucose monitoring (CGM) system. A CGM system measures glucose levels throughout the day and can be very useful in the management of diabetes. Some analyte monitoring systems use measurements indicative of analyte levels in interstitial fluid ("ISF") to calculate ISF analyte levels and then convert the ISF analyte levels to blood analyte levels. The analyte monitoring systems may display the blood analyte levels to a user. However, because ISF analyte levels lag behind blood analyte levels, accurate conversion of ISF analyte levels to blood analyte levels is difficult.

SUMMARY

Aspects of the present invention relate to improving the accuracy of blood analyte levels displayed to a user.

One aspect of the invention may provide a sensor configured for at least partial placement in an analyte-containing medium. In some embodiments, the sensor may include a first transducer that exhibits one or more detectable properties based on an amount or concentration of an analyte in proximity to the first transducer. In some embodiments, the sensor may include a first diffusion barrier arranged such that, when the sensor is placed in the medium, analyte contained in the medium diffuses through the first diffusion barrier before reaching the first transducer, wherein the first diffusion barrier is configured such that analyte contained in the medium diffuses through the first diffusion barrier at a first diffusion rate $r_1$. In some embodiments, the sensor may include a second transducer that exhibits one or more detectable properties based on an amount or concentration of an analyte in proximity to the second transducer. In some embodiments, when the sensor is placed in the medium, diffusion of analyte contained in the medium to the first transducer may delayed relative to diffusion of analyte contained in the medium to the second transducer.

In any of the above embodiments, the sensor may include a second diffusion barrier arranged such that, when the sensor is placed in the medium, analyte contained in the medium may diffuse through the second diffusion barrier before reaching the second transducer. In some embodiments, the second diffusion barrier is configured such that analyte contained in the medium diffuses through the second diffusion barrier at a second diffusion rate $r_2$, wherein $r_2$ is greater than $r_1$.

In any of the above embodiments, the first diffusion barrier may comprise an outer surface configured to be disposed adjacent the analyte-containing medium, an inner surface disposed opposite the outer surface and adjacent the first transducer, and a first thickness defined between the outer surface and the inner surface of the first diffusion barrier. In some embodiments, the second diffusion barrier may comprise an outer surface configured to be disposed adjacent the analyte-containing medium, an inner surface disposed opposite the outer surface and adjacent the second transducer, and a second thickness defined between the outer surface and the inner surface of the second diffusion barrier. In some embodiments, the second thickness may be greater than the first thickness such that when the sensor is placed in the medium, analyte diffusing from the medium will exhibit a greater lag time diffusing through the second diffusion barrier than through the first diffusion barrier.

In any of the above embodiments, the first diffusion barrier may be disposed over the first transducer, and the first diffusion barrier may be configured such that, when the sensor is placed in the medium, the first diffusion barrier at least partially inhibits diffusion of analyte to the second transducer.

In any of the above embodiments, the second diffusion barrier may be disposed over the second transducer, and the second diffusion barrier may be configured such that, when the sensor is placed in the medium, the second diffusion barrier at least partially inhibits diffusion of analyte to the second transducer, and the first diffusion barrier inhibits diffusion of analyte to a greater degree than the second diffusion barrier.

In any of the above embodiments, the sensor may include a third transducer that exhibits one or more detectable properties based on an amount or concentration of an analyte in proximity to the third transducer. In some embodiments, the sensor may further include a third diffusion barrier arranged such that, when the sensor is placed in the medium, analyte contained in the medium may diffuse through the third diffusion barrier before reaching the third transducer. In some embodiments, the third diffusion barrier may be configured such that analyte contained in the medium diffuses through the third diffusion barrier at a third diffusion rate $r_3$, wherein $r_1$ is greater than $r_3$.

In any of the above embodiments, the second transducer may be arranged such that, when the sensor is placed in the medium, analyte contained in the medium need not diffuse through a diffusion barrier before reaching the second transducer.

In a second aspect, which may be combinable with features of any of the above embodiments, an analyte detection system may include a sensor configured for at least partial placement in an interstitial fluid. In some embodiments, the sensor may include a first transducer that exhibits one or more detectable properties based on an amount or concentration of an analyte in proximity to the first transducer. In some embodiments, the sensor may include a first diffusion barrier arranged such that when the sensor is placed in the interstitial fluid, analyte contained in the interstitial fluid may diffuse through the first diffusion barrier before reaching the first transducer. In some embodiments, the first transfusion barrier may be configured such that analyte contained in the interstitial fluid diffuses through the first diffusion barrier at a first diffusion rate $r_1$. In some embodiments, the sensor may include a second transducer that exhibits one or more detectable properties based on an amount or concentration of an analyte in proximity to the second transducer element. In embodiments, the system may include a transceiver configured to receive first sensor data collected from the first transducer. In some embodiments, the transceiver may be configured to receive second sensor data collected from the second transducer. In some embodiments, the transceiver may be configured to calculate an interstitial fluid analyte level rate of change based on at least the first sensor data, the second sensor data, and $r_1$.

In any of the above embodiments of the second aspect, the system may comprising a second diffusion barrier arranged such that when the sensor is placed in the interstitial fluid, analyte contained in the interstitial fluid may diffuse through the second diffusion barrier before reaching the first transducer. In some embodiments, the second transfusion barrier may be further configured such that analyte contained in the interstitial fluid diffuses through the second diffusion barrier at a second diffusion rate $r_2$, $r_2$ being greater than $r_1$. In embodiments, calculating the interstitial fluid analyte level rate of change may be further based on $r_2$.

In a third aspect, which may be combinable with features of any of the above embodiments, a method for detecting the rate of change of an analyte concentration in a medium may be provided. In some embodiments, the method may include receiving from a sensor at least first sensor data corresponding to a first measurement of a detectable property exhibited by a first transducer and second sensor data corresponding to a second measurement of a detectable property exhibited by a second transducer. In some embodiments, the first sensor data may be indicative of an amount or concentration of an analyte in proximity to the first transducer after passing through a first diffusion barrier. In some embodiments, the method may include calculating an analyte level rate of change based on at least the first sensor data, the second sensor data, and a first diffusion rate $r_1$ of the analyte through the first diffusion barrier.

In any of the above embodiments of the third aspect, a detectable property exhibited by the second transducer may be indicative of an amount or concentration of the analyte in proximity to the second transducer after passing through a second diffusion barrier. In some embodiments, calculating the analyte level rate of change may be further based on a second diffusion rate $r_2$ of the analyte through the second diffusion barrier, $r_2$ being greater than $r_1$.

In any of the above embodiments of the third aspect, the method may include calculating an interstitial fluid analyte level based on at least one of the first sensor data and the second sensor data. In some embodiments, the method may include calculating a blood analyte level based on the interstitial fluid analyte level and the analyte level rate of change.

In any of the above embodiments of the third aspect, the method may include detecting that a transceiver is positioned within a proximity of the sensor. In some embodiments, the method may include transmitting, in response to detecting that the transceiver is proximate the sensor, from the transceiver to the sensor power sufficient to perform the first measurement and the second measurement, the transmitted power being used to perform the first measurement and the second measurement. In some embodiments, the method may include removing the transceiver from the proximity of the sensor. In some embodiments, this removing step may occur after receiving from the sensor the first sensor data and the second sensor data, and before additional measurements are performed.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
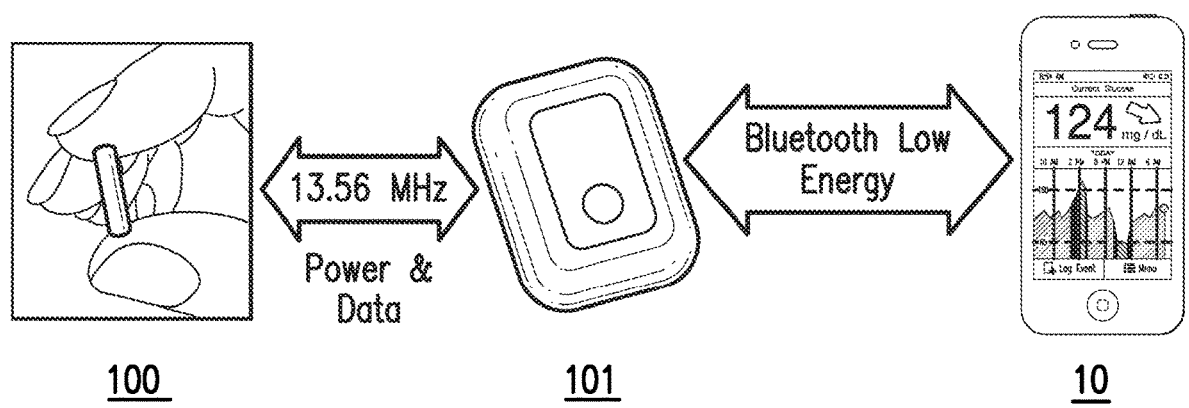
FIG. 1 is a schematic view of an analyte monitoring system embodiment, which includes an implantable sensor and a transceiver.

FIG. 1 is a schematic view of an analyte monitoring system embodying aspects of the present invention. In one non-limiting embodiment, the system includes a sensor 100 and an external transceiver 101. In the embodiment shown in FIG. 1, the sensor 100 is implanted in a living animal (e.g., a living human). The sensor 100 may be implanted, for example, in a living animal's arm, wrist, leg, abdomen, or other region of the living animal suitable for sensor implantation. For example, as shown in FIG. 1, in one non-limiting embodiment, the sensor 100 may be implanted between the skin and subcutaneous tissues. In some embodiments, the sensor 100 may be an optical sensor. In some embodiments, the sensor 100 may be a chemical or biochemical sensor.

Figure 12:
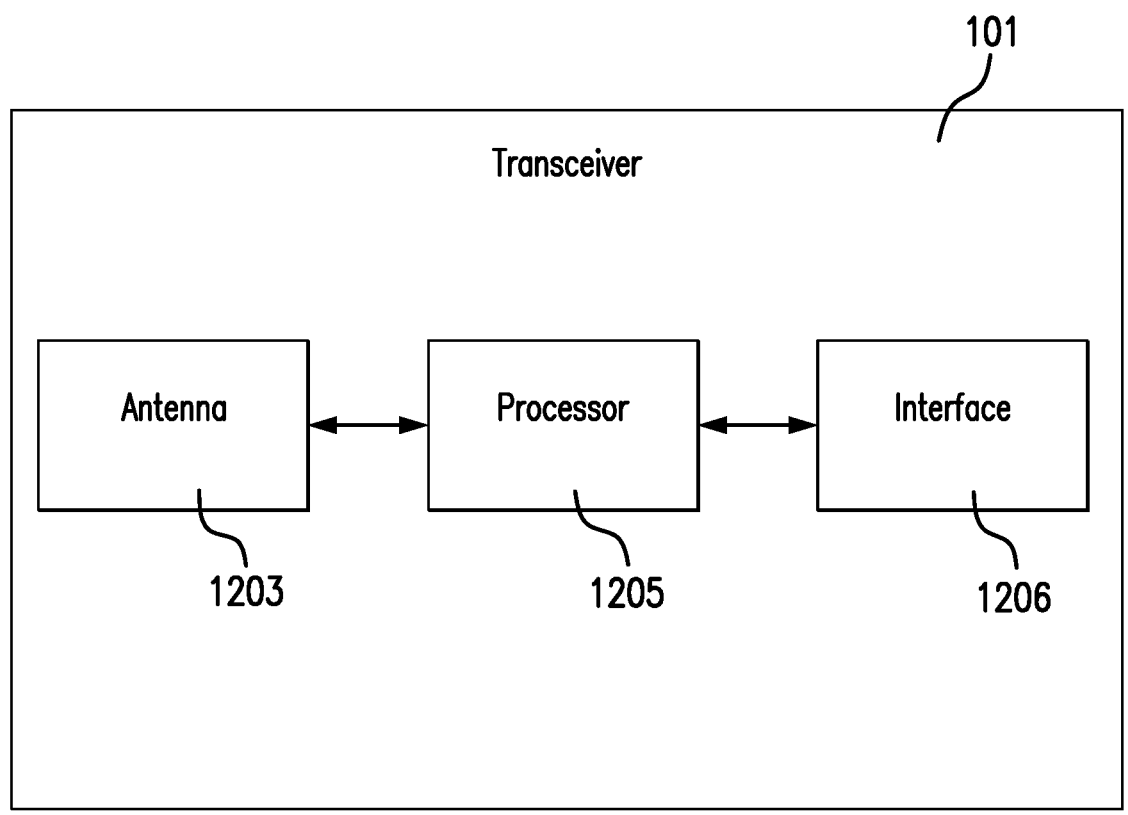
FIG. 12 is a schematic diagram of a transceiver according to aspects of the present invention.

In some embodiments, as illustrated in FIG. 1 and FIG. 12, the transceiver 101 may be an electronic device that communicates with the sensor 100 to power the sensor 100 and/or obtain analyte (e.g., glucose) readings from the sensor 100. In some non-limiting embodiments, the transceiver 101 may be a handheld reader, a wristwatch, waistband, armband, keychain attachment, or it may be incorporated within or a component of a user device 10 (e.g., a smartphone, personal data assistant, handheld device, or laptop computer). In other non-limiting embodiments, the transceiver 101 may be held on a user's body by adhesive (e.g., as part of a biocompatible patch). In some embodiments, positioning (i.e., hovering or swiping/waiving/passing) the transceiver 101 within range over the sensor implant site (i.e., within proximity of the sensor 100) may cause the transceiver 101 to automatically convey a measurement command to the sensor 100 and receive a reading from the sensor 100.

Figure 11:
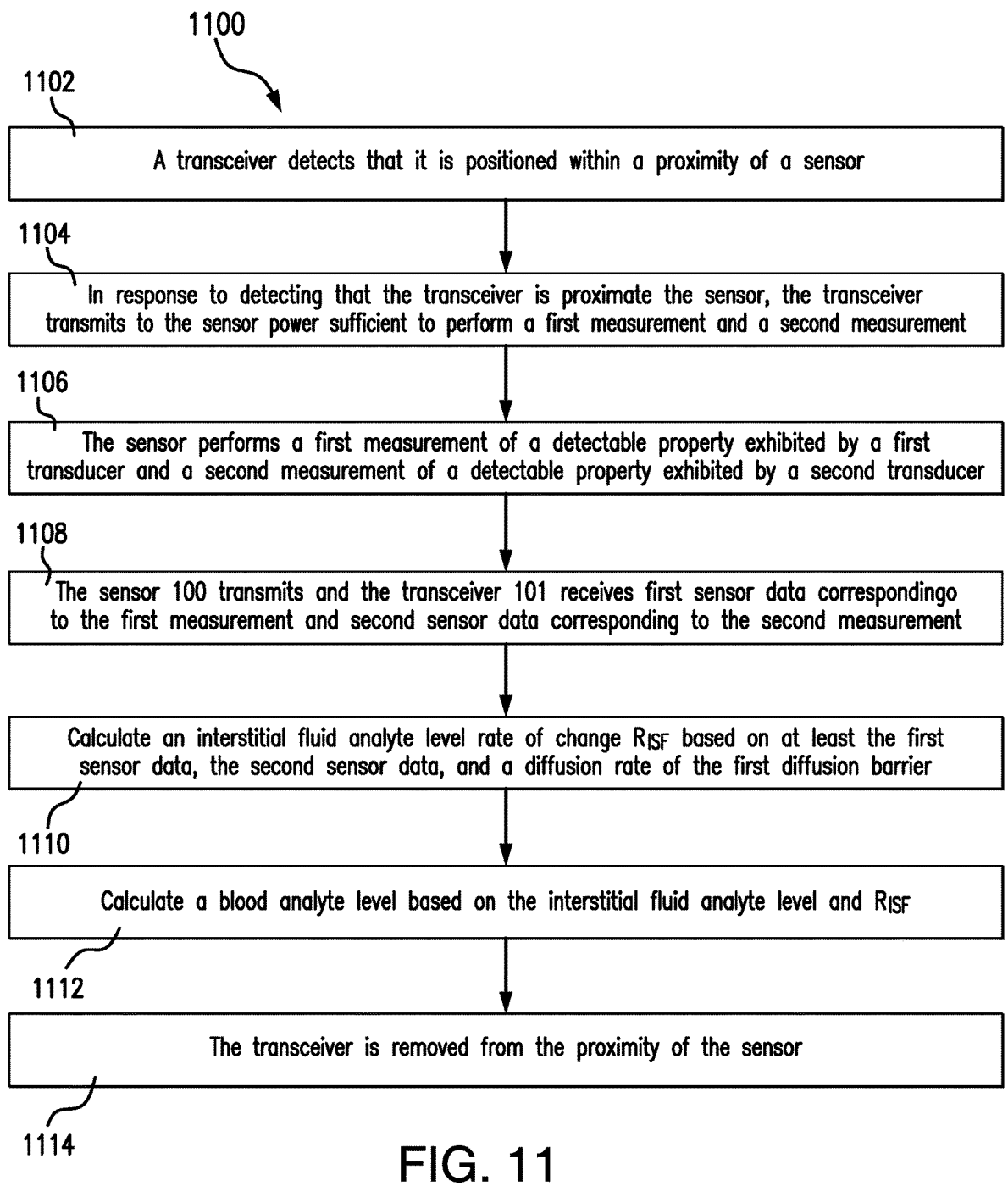
FIG. 11 is a flow chart illustrating a process for calculating analyte levels embodying aspects of the present invention.

In some embodiments, as shown in FIG. 12, the transceiver 101 may include one or more of an antenna 1203 and a processor 1205. The processor 1205 may perform one or more of steps 1102, 1104, 1110, and 1112 as illustrated in FIG. 11 and discussed below. In some embodiments, the transceiver may include a user interface 1207. In one non-limiting embodiment, the user interface 1207 may include one or more of a liquid crystal display (LCD) and vibration motor, but, in other embodiments, different types of user interfaces may be used, or the transceiver 101 may not include a user interface.

In some embodiments, the antenna 1203 may include an inductive element, such as, for example, a coil. In some embodiments, the antenna 1203 may generate an electromagnetic wave or electrodynamic field (e.g., by using a coil) to induce a current in an inductive element of the sensor 100, which may power the sensor 100 via an inductive element (e.g., inductive element 114 of FIGS. 2-3) disposed in the sensor 100 and configured to receive and/or transmit electromagnetic waves or electrodynamic fields from and/or to the transceiver antenna 1203. In some embodiments, the antenna 1203 may additionally or alternatively convey data (e.g., commands) to the sensor 100. For example, in a non-limiting embodiment, the antenna 1203 may convey data by modulating the electromagnetic wave used to power the sensor 100 (e.g., by modulating the current flowing through a coil of the antenna 1203). The modulation in the electromagnetic wave generated by the transceiver 101 may be detected/extracted by the sensor 100. Moreover, the antenna 1203 may receive data (e.g., measurement information) from the sensor 100. For example, in a non-limiting embodiment, the antenna 1203 may receive data by detecting modulations in the electromagnetic wave generated by the sensor 100, e.g., by detecting modulations in the current flowing through the coil of the antenna 1203.

The inductive element of the transceiver 101 and the inductive element (e.g., inductive element 114 illustrated in FIGS. 2-3) of the sensor 100 may be in any configuration that permits adequate field strength to be achieved when the two inductive elements are brought within adequate physical proximity.

In some embodiments, the processor 1205 may calculate one or more analyte concentrations based on the analyte readings received from the sensor 100. In some embodiments, the processor 1205 may also generate one or more alerts and/or alarms based on the calculated analyte concentrations (e.g., if the calculated analyte concentration exceeds or falls below one or more thresholds). The calculated analyte concentrations, alerts, and/or alarms may be communicated (e.g., displayed) via the user interface 1207.

In some embodiments, the transceiver 101 may communicate (e.g., using a wireless communication standard, such as, for example and without limitation, Bluetooth) with a user device (e.g., a smartphone, personal data assistant, handheld device, or laptop computer). In other embodiments, the transceiver 101 may be incorporated within or a component of a user device. In some embodiments, the user device may receive calculated analyte concentrations, alerts, and/or alarms from the transceiver 101 and display them. Display by the user device may be in addition to, or in the alternative to, display by the user interface 1207 of the transceiver 101. For example, in some embodiments, as illustrated in FIG. 1, the transceiver 101 may include a user interface 1207, but this is not required. In some alternative embodiments, the transceiver 101 may not have a user interface 1207, and calculated analyte concentrations, alerts, and/or alarms may instead be displayed by a user device. In other embodiments, the transceiver 101 may be incorporated within or a component of a user device, and the transceiver 101 and user device may share a user interface and/or display.

In some non-limiting embodiments, the transceiver 101 and sensor 100 may have some or all of the structure described in U.S. Pat. Nos. 9,414,775 and 9,427,182, which are incorporated by reference in their entireties.

Figure 2:
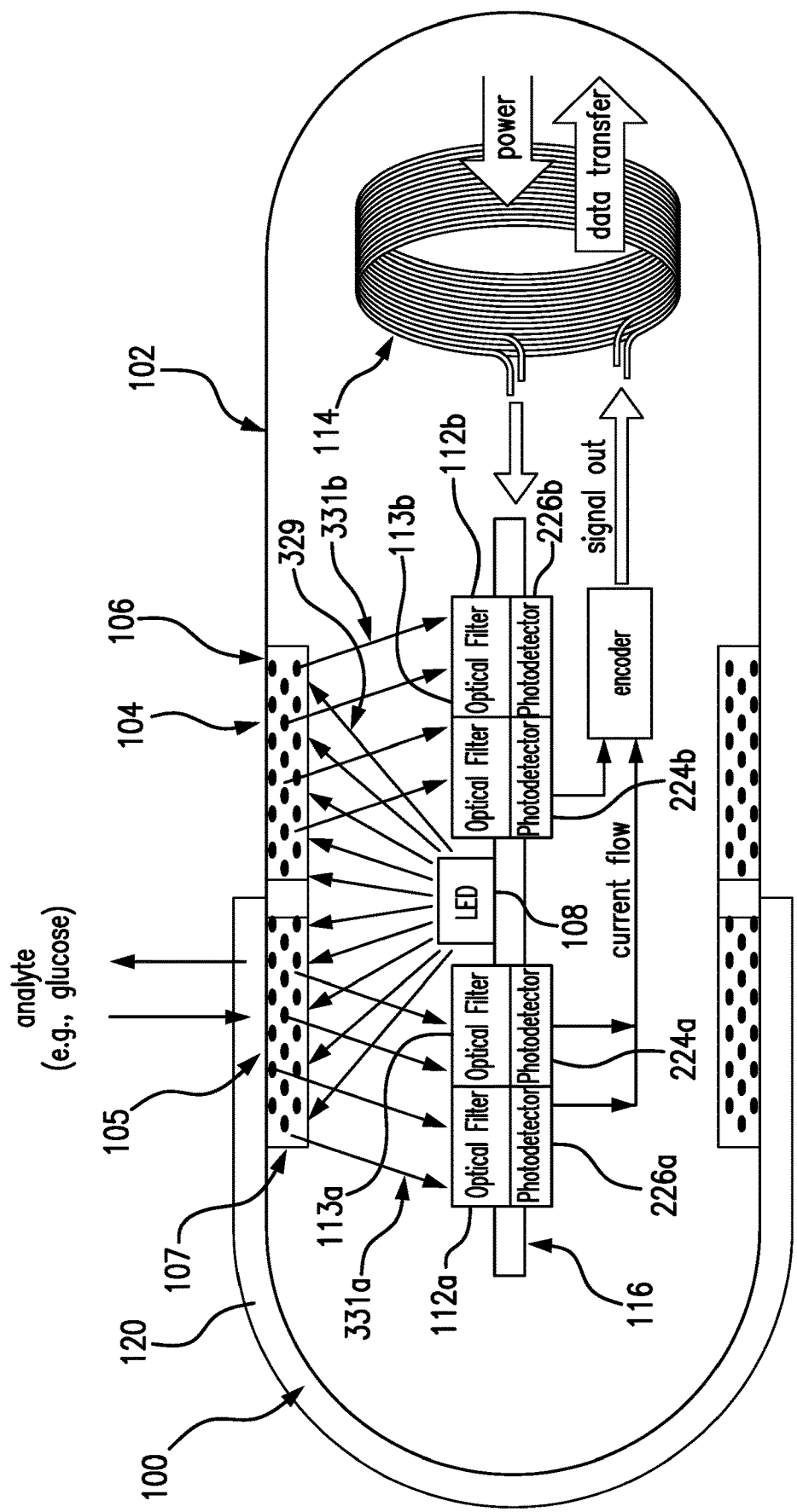
FIG. 2 illustrates a longitudinal view of a sensor embodying aspects of the present invention.
Figure 3:
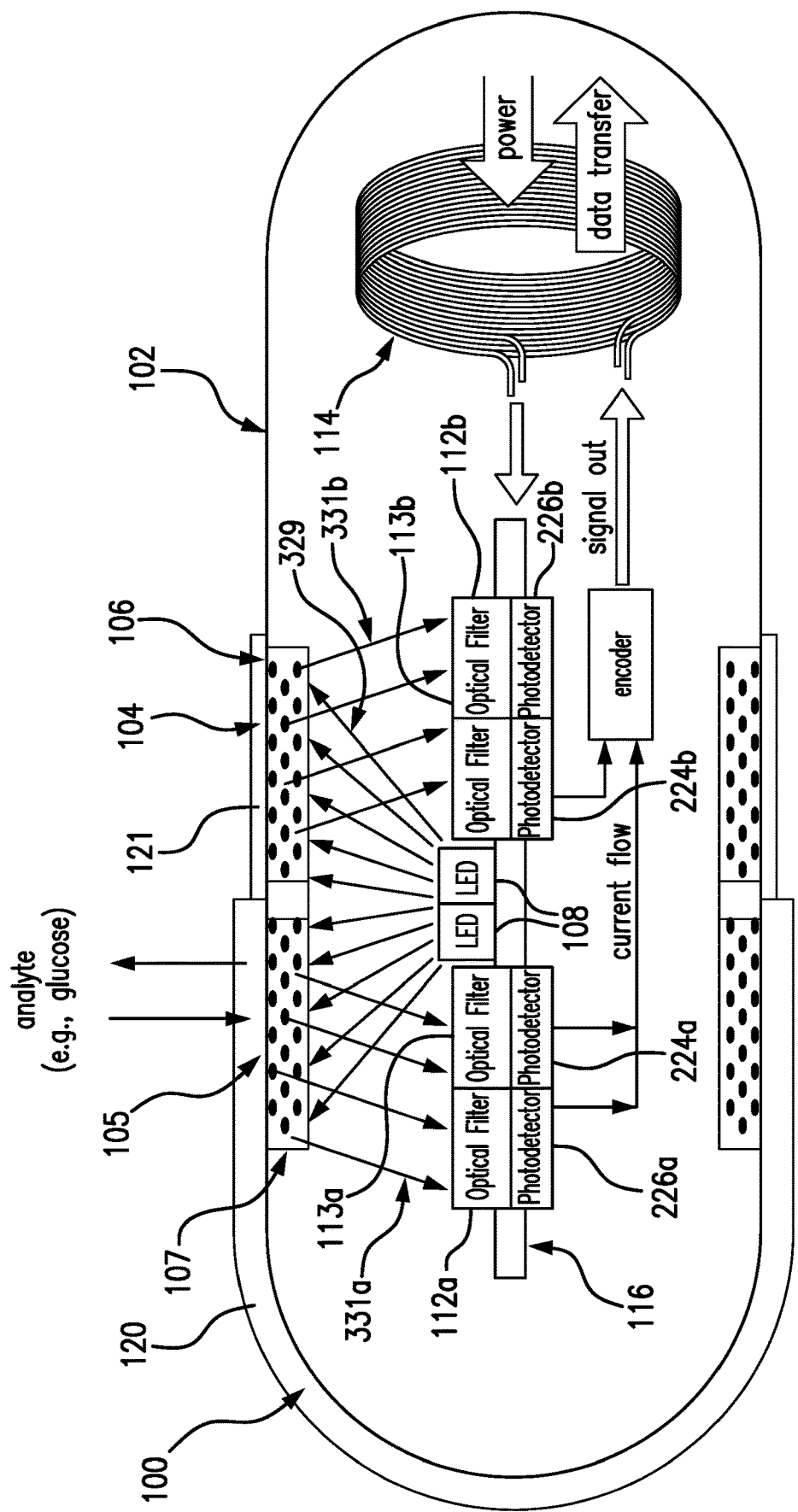
FIG. 3 illustrates a longitudinal view of a sensor embodying aspects of the present invention.

FIGS. 2-3 illustrate aspects of non-limiting examples of a sensor 100 that may be used in the analyte monitoring system illustrated in FIG. 1. In some embodiments, the sensor 100 may be an optical sensor. In one non-limiting embodiment, sensor 100 includes a sensor housing 102 (i.e., body, shell, or capsule). In exemplary embodiments, sensor housing 102 may be formed from a suitable, optically transmissive polymeric material, such as, for example, acrylic polymers (e.g., polymethylmethacrylate (PMMA)).

In some embodiments, the sensor 100 may include one or more of a first transducer 107 and a second transducer 106. In some embodiments, the first transducer 107 may include one or more first indicator molecules 105. In some non-limiting embodiments, the second transducer 106 may include one or more second indicator molecules 104. In some embodiments, the first and second indicator molecules 105, 104 may be fluorescent indicator molecules or absorption indicator molecules. In some non-limiting embodiments, the first and second indicator molecules 105, 104 may be as described in U.S. Pat. No. 6,344,360 or 9,414,775, which are incorporated herein by reference in their entireties. In some non-limiting embodiments, one or more of the transducers 106, 107 may include a polymer graft (e.g., matrix layer or hydrogel) coated or embedded on or in at least a portion of the exterior surface of the sensor housing 102. In some non-limiting embodiments, first and second indicator molecules 105, 104 may be distributed throughout the polymer graft. In some embodiments, the first and second transducers 107, 106 may be embedded within the sensor housing 102. In some embodiments, the first and second transducers 107, 106 may cover the entire surface of sensor housing 102 or only one or more portions of the surface of housing 102. In some non-limiting embodiments, the first indicator molecules 105 may be distributed throughout the entire first transducer 107 or only throughout one or more portions of the first transducer 107. In some non-limiting embodiments, the second indicator molecules 104 may be distributed throughout the entire second transducer 106 or only throughout one or more portions of the second transducer 106.

Figure 4:
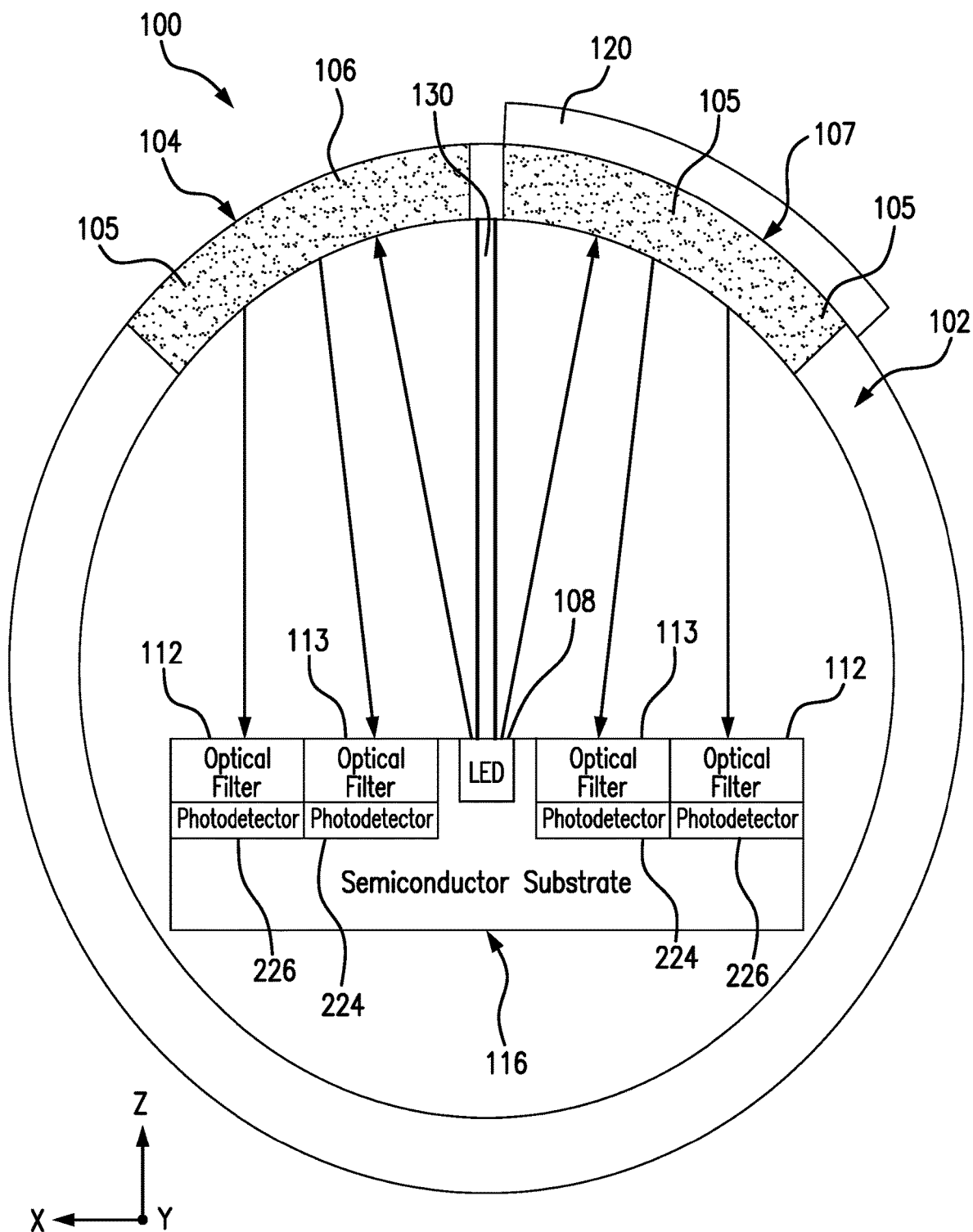
FIG. 4 illustrates a cross-sectional view of a sensor embodying aspects of the present invention.

In some embodiments, as shown in FIGS. 2-4, the sensor 100 may include one or more light sources 108, which may be, for example, a light emitting diode (LED) or other light source that emits light over a range of wavelengths that interact with the first and second indicator molecules 105, 104. In some embodiments, the second indicator molecules 104 may be chemically identical to first indicator molecules 105, and/or may interact with and/or emit the same or similar wavelengths of light. In other embodiments, the second indicator molecules 104 may differ from the first indicator molecules 105, and/or may interact with and/or emit different wavelengths of light.

In some embodiments, the sensor 100 may include one or more photodetectors 224, 226 (e.g., photodiodes, phototransistors, photoresistors, or other photosensitive elements). In some embodiments, the one or more photodetectors of the sensor 100 may include one or more signal photodetectors 226 that may be sensitive to emission light (e.g., fluorescent light) emitted by the indicator molecules 104, 105 such that a signal may be generated by the photodetectors 224 in response thereto that is indicative of the level of the indicator molecules 104, 105 and, thus, the concentration of analyte of interest (e.g., glucose). In some embodiments, as shown in FIGS. 2-4, the one or more signal photodetectors 226 may include at least one first signal photodetector 226a configured to receive first emission light 331a emitted by the first indicator molecules 105 of the first transducer 107 and to output a signal indicative of an amount thereof. In some embodiments, as shown in FIGS. 2-4, the one or more signal photodetectors 226 may include at least one second signal photodetector 226b configured to receive second emission light 331b light emitted by the second indicator molecules 104 of the second transducer 106 and to output a signal indicative of an amount thereof.

In some embodiments, the one or more photodetectors of the sensor 100 may include one or more reference photodetectors 224 that may be sensitive to excitation light 329 (e.g., ultraviolet light) emitted by the one or more light sources 108 such that a signal may be generated by the photodetectors 226 in response thereto that is indicative of an amount of excitation light 329 reflected by the first and second transducers 107, 106. In some embodiments, as shown in FIGS. 2-4, the one or more reference photodetectors 226 may include at least one first reference photodetector 224a configured to receive excitation light 329 reflected by the first transducer 107 and to output a signal indicative of an amount thereof. In some embodiments, as shown in FIGS. 2-4, the one or more reference photodetectors 224 may include at least one second reference photodetector 224b configured to receive excitation light 329 reflected by the second transducer 106 and to output a signal indicative of an amount thereof.

As illustrated in FIGS. 2-4, some embodiments of sensor 100 include one or more optical filters 112a, 112b, 113a, 113b, such as high pass or band pass filters, and the sensor 100 may be configured such that light passes through an optical filter 112a, 112b, 113a, or 113b before reaching a photosensitive side of the one or more photodetectors 224a, 224b, 226a, 226b. In some non-limiting embodiments, the one or more optical filters 112a, 112b, 113a, 113b may cover a photosensitive side of the one or more photodetectors 224a, 224b, 226a, 226b, respectively.

In some embodiments, sensor 100 may be wholly self-contained. In other words, the sensor may be constructed in such a way that no electrical leads extend into or out of the sensor housing 102 to supply power to the sensor (e.g., for driving a light source 108) or to convey signals from the sensor 100. In some non-limiting embodiments, the sensor 100 may be powered by an external power source (e.g., external transceiver 101). For example, the external power source may generate a magnetic field to induce a current in an inductive element 114 (e.g., a coil or other inductive element). In some embodiments, the sensor 100 may use the inductive element 114 to communicate information to an external sensor reader (e.g., transceiver 101). In some embodiments, the external power source and data reader may be the same device (e.g., transceiver 101). In some embodiments, an antenna 1203 of transceiver 101 may be arranged as a coil that wraps around the sensor 100. In other embodiments, the sensor may have a different configuration, such as, for example, those described in U.S. patent application Ser. No. 13/650,016, which is incorporated herein by reference in its entirety, with particular reference to FIGS. 2A-2C, or those described in U.S. Pat. No. 9,414,775, which is incorporated herein by reference in its entirety.

In some embodiments, the sensor 100 may include a substrate 116. In some non-limiting embodiments, the substrate 116 may be a semiconductor substrate and circuitry may be fabricated in the semiconductor substrate 116 (see FIG. 4). In some embodiments, the circuitry may include analog and/or digital circuitry. In some embodiments, the circuitry may incorporate some or all of the structure described in U.S. patent application Ser. No. 13/650,016, which is incorporated herein by reference in its entirety, with particular reference to FIG. 11D. Although in some embodiments the circuitry may be fabricated in the semiconductor substrate 116, in alternative embodiments, a portion or all of the circuitry may be mounted or otherwise attached to the semiconductor substrate 116. In other words, in alternative embodiments, a portion or all of the circuitry may include discrete circuit elements, an integrated circuit (e.g., an application specific integrated circuit (ASIC)) and/or other electronic components discrete and may be secured to the semiconductor substrate 116, which may provide communication paths between the various secured components. In some alternative embodiments, the substrate 116 may be a printed circuit board.

In some embodiments, the one or more photodetectors 224, 226 may be mounted on the semiconductor substrate 116, but, in some embodiments, as shown in FIG. 4, the one or more photodetectors 224, 226 may be fabricated in the semiconductor substrate 116. In some embodiments, the one or more light sources 108 may be mounted on the semiconductor substrate 116. For example, in a non-limiting embodiment, the light source(s) 108 may be flip-chip mounted on the semiconductor substrate 116. However, in some embodiments, the light source(s) 108 may be fabricated in the semiconductor substrate 116.

According to one aspect of the invention, the sensor 100 may be configured to measure various biological analytes in the living body of an animal (including a human). For example, sensor 100 may be used to measure glucose, oxygen toxins, pharmaceuticals or other drugs, hormones, and other metabolic analytes in, for example, the human body. The specific composition of the transducers 106, 107 and the indicator molecules 104, 105 therein may vary depending on the particular analyte the sensor is to be used to detect and/or where the sensor is to be used to detect the analyte (i.e., in interstitial fluid). The transducers 106, 107 may facilitate exposure of the indicator molecules 104, 105 to the analyte. The optical characteristics of the indicator molecules (e.g., the level of fluorescence of fluorescent indicator molecules) may be a function of the concentration of the specific analyte to which the indicator molecules are exposed.

In some embodiments, one or more the light sources 108 may be positioned to emit excitation light 329 that travels within the sensor housing 102 and reaches the first and second indicator molecules 105, 104 of the first and second transducers 107, 106, respectively. In some embodiments, the photodetectors 224a, 226a, which may be located beneath filters 112a, 113a, may be positioned to receive light from the first indicator molecules 105 of the first transducer 107. In some embodiments, the photodetectors 224b, 226b, which may be located beneath filters 112b, 113b, may be positioned to receive light from the second indicator molecules 104 of the second transducer 106.

In operation, as shown in FIGS. 2-4, the light source(s) 108 may emit excitation light 329 that travels within the sensor housing 102 and reaches the first and second indicator molecules 104, 105 of the first and second transducers 106, 107. In a non-limiting embodiment, the excitation light 329 may cause the indicator molecules 104, 105 distributed in transducers 106, 107 to emit light (e.g., to fluoresce). In some embodiments, the transducers 106, 107 may be permeable to the analyte (e.g., glucose) in the medium (e.g., blood or interstitial fluid) into which the sensor 100 is implanted. Accordingly, in some embodiments, the first and second indicator molecules 105, 104 in the first and second transducers 107, 106, respectively, may interact with the analyte in the medium and, when irradiated by the excitation light 329, may emit first and second emission light 331a, 331b, respectively, which may be indicative of the presence and/or concentration of the analyte in the medium. In some embodiments, the one or more of the first and second emission light 331a and 331b may be, for example and without limitation, fluorescent light.

In some embodiments, the photodetectors 224, 226 may receive light. In some embodiments, the one or more photodetectors 224 may be covered by filters 112, and the one or more photodetectors 226 may be covered by filters 113. In some embodiments, the filters 112, 113 may allow only a certain subset of wavelengths of light to pass through. In some embodiments, the filters 112, 113 may be thin film (e.g., dichroic) filters deposited on glass, and the filters 112, 113 may pass only a narrow band of wavelengths and otherwise reflect (or absorb) the remaining light. In some embodiments, the filters 112, 113 may be identical (e.g., each filter 112, 113 may allow signal light to pass) or different (e.g., filters 112 may allow signal light to pass, and filters 113 may allow reference light to pass). In some embodiments where the first and second indicator molecules 105, 104 emit light at different wavelengths, the signal light filter 112a may be configured to pass light 331a emitted by the first indicator molecules 105 to the first signal photodetector 226a but to reflect (or absorb) the excitation light 329 and the light 331b emitted by the second indicator molecules 104. Similarly, the signal light filter 112b may be configured to pass light 331b emitted by the second indicator molecules 104 to the second signal photodetector 226b but to reflect (or absorb) the excitation light 329 and the light 331a emitted by the first indicator molecules 105. In this manner, the first and second signal photodetectors 226a and 226b disposed under the signal light filters 112a and 112b, respectively, may be selected to receive only a respective one of light 331a and 331b emitted by the first and second indicator molecules 104, 105 of the first and second transducer 107, 106, respectively.

In some embodiments, the filters 113 may pass light at the same wavelength as the wavelength of the excitation light 329 emitted from the light source 108 (e.g., 378 nm). In some embodiments, first indicator molecules 105 and second indicator molecules 104 may be excited by light emitted at different wavelengths. In such embodiments, multiple (e.g., two) light sources 108 may be provided, wherein one light source 108 emits light at a wavelength capable of exciting indicator molecules 105, and a second light source 108 emits light at a wavelength capable of exciting indicator molecules 104.

Photodetectors 226a, 226b may be signal photodetectors that detect the amount of fluoresced light 331 that is emitted from the first and second indicator molecules 104, 105 in the first and second transducers 106, 107. In some non-limiting embodiments, the signal filters 112a, 112b—which may in some embodiments cover photodetectors 224a, 224b—may pass light in the range of about 400 nm to 500 nm. Higher analyte levels may correspond to a greater amount of fluorescence of the molecules 105, 106 in the transducers 106, 107, and therefore, a greater amount of photons striking the signal photodetectors 226.

As illustrated in FIGS. 2-4, a diffusion barrier 120 may be disposed on or over a portion of the sensor body 102. In some embodiments, the diffusion barrier 120 may be formed as a membrane, graft, mesh, sputtered layer, or any other structural arrangement configured to permit at least partial diffusion of analyte therethrough. When the sensor 100 is implanted, for example in a medium such as interstitial fluid, analyte may diffuse through the diffusion barrier 120 before reaching the transducer 107. The diffusion barrier 120 may have an associated diffusion rate r, which may represent the rate at which analyte may diffuse across the diffusion barrier 120. The diffusion barrier 120 may further have an associated lag time $\tau$, which may represent the time for analyte to diffuse across the diffusion barrier 120. The lag time $\tau$ and diffusion rate r may be inversely related (e.g., $\tau$ may be equal to 1/r). Values for both lag time $\tau$ and diffusion rate r may be determined or measured in advance through quality assurance or testing practices.

In some embodiments, such as that illustrated in FIG. 2, only one transducer 107 is covered by a diffusion barrier 120. In this manner, analyte in the medium will reach the transducer 107 at a delay (which may correspond to lag time $\tau$) relative to when it reaches transducer 106. Thus, signal received from the transducer 106 may be indicative of current analyte levels proximate the sensor 100, and signal received from the transducer 107 may be indicative of analyte levels proximate the sensor 100 at a time period (which may correspond to lag time $\tau$) prior to the time at which the measurement signal is received. By comparing the measurements from the transducers 106, 107, an analyte level rate of change proximate the sensor 100 may be calculated. In some embodiment, this rate of change may be calculated based on measurement data received from the first transducer 107, measurement data received from the second transducer 106, and the diffusion rate r and/or lag time $\tau$ of the diffusion barrier 120.

In other exemplary embodiments, as illustrated in FIG. 3, the first transducer 107 may be covered by a first diffusion barrier 120, and the second transducer 106 may be covered by a second diffusion barrier 121. The first and second diffusion barriers 120 and 121 may have different diffusion characteristics. For example, the first diffusion barrier 120 may have a first diffusion rate $r_1$ and a first lag time $\tau_1$, and the second diffusion barrier 121 may have a second diffusion rate $r_2$ and a second lag time $\tau_2$, each different than the respective values for the diffusion barrier 120. Values for the diffusion rates and lag times may be determined or measured in advance through quality assurance or testing practices. Signal received from the first transducer 107 may be indicative of analyte levels proximate the sensor 100 at a time period (which may correspond to lag time $\tau_1$) prior to the time at which the measurement signal is received, and signal received from the second transducer 106 may be indicative of analyte levels proximate the sensor 100 at a time period (which may correspond to lag time $\tau_2$) prior to the time at which the measurement signal is received. By comparing the measurements from the first and second transducers 107, 106, an analyte level rate of change proximate the sensor 100 may be calculated. In some embodiment, this rate of change may be calculated based on measurement data received from the first transducer 107, measurement data received from the second transducer 106, the diffusion rate $r_1$ and/or lag time $\tau_1$ of the diffusion barrier 120, and the diffusion rate $r_2$ and/or lag time $\tau_2$ of the diffusion barrier 121.

A difference between the diffusion rates (and lag times) of the diffusion barriers 120, 121 may be effected by varying any of a variety of characteristics of the respective diffusion barriers 120, 121. For example, as illustrated in FIG. 3, the diffusion barriers 120, 121 may have different thicknesses. In other embodiments, the diffusion barriers 120, 121 may have different porosities or structural characteristics (e.g., channels) allowing passage of analyte. In still other embodiments, the diffusion barriers 120, 121 may have different chemical compositions, such that one of the barriers may be more or less hydrophobic or hydrophilic than the other. Other arrangements for controlling the diffusion rates of the diffusion membranes may be used.

Figure 10:
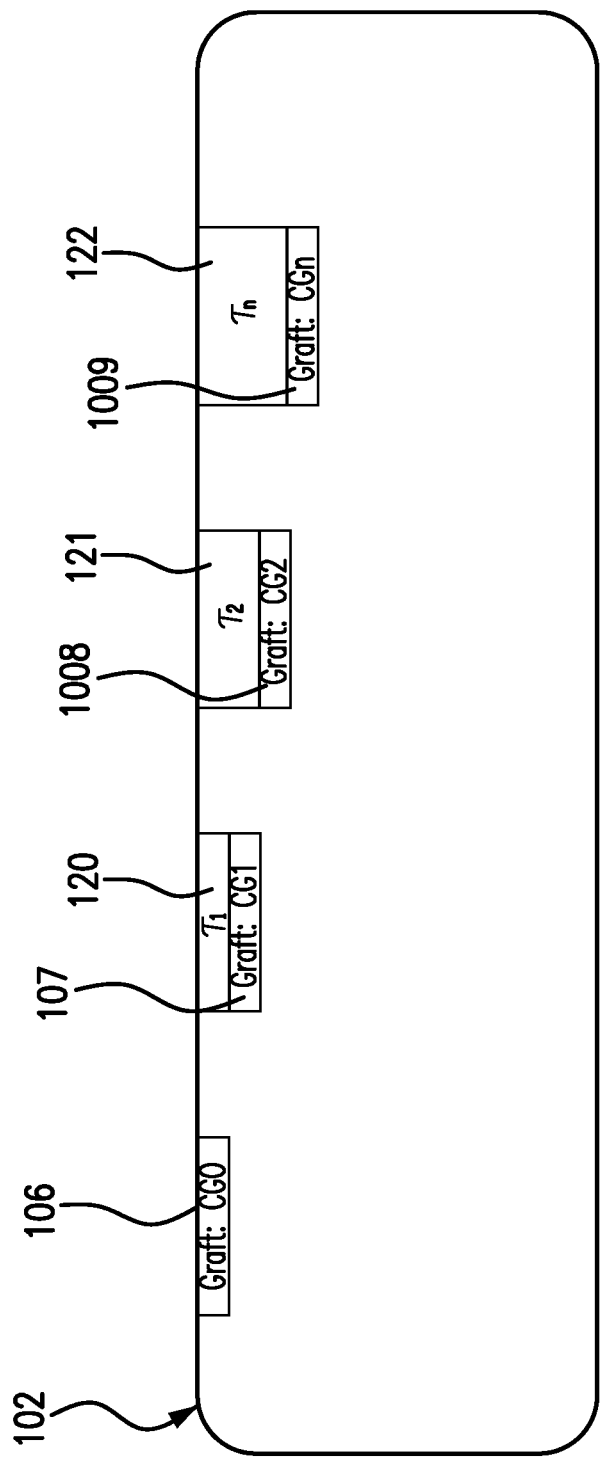
FIG. 10 illustrates a schematic diagram of a sensor having multiple diffusion barriers according to aspects of the present invention.

Although one diffusion barrier 120 is shown in FIGS. 2 and 4 and two diffusion barriers 120 and 121 are shown in FIG. 3, in some embodiments, the sensor 100 may include more than two diffusion barriers. For example, as shown in FIG. 10, the sensor 100 may include first, second, and third diffusion barriers 120, 121, and 122, each with differing diffusion characteristics. In other embodiments, the sensor 100 may have more than three diffusion barriers with differing diffusion characteristics.

Similarly, although two transducers 106 and 107 are shown in FIGS. 2-4, in some embodiments, the sensor 100 may include more than two transducers. For example, as shown in FIG. 10, the sensor 100 may include first, second, third, and fourth transducers 107, 106, 1008, and 1009. In some embodiments, the sensor 100 may use the additional transducers with additional diffusion barriers to measure simultaneously analyte levels at additional lag times. In some embodiments, the transceiver 101 may use these additional measurements to obtain a more accurate estimate for the analyte level rate of change proximate the sensor body 102. In some non-limiting embodiments, the transceiver 101 perform non-linear regression to calculate the analyte level rate of change using the differently delayed analyte levels.

As illustrated in FIGS. 3 and 4, the transducers 106, 107 may be axially arranged along the length of the sensor body 102, such that the transducer 107 is disposed along a first axial portion of the sensor body 102, and the transducer 106 is disposed along a second axial portion of the sensor body 102, the first axial portion being different than the first. The photodetectors 224, 226 and optical filters 112, 113 may also be axially arranged, such that the photodetectors 224, 226 and optical filters 112, 113 for measuring signal from the transducer 107 may be disposed along the first axial portion of the sensor body 102, and the photodetectors 224, 226 and optical filters 112, 113 for measuring signal from the transducer 106 may be disposed along the second axial portion of the sensor body 102.

FIG. 4 shows a cross-sectional view of another exemplary embodiment of a sensor 100. In some embodiments, as illustrated in FIG. 4, the transducers 106, 107 may be circumferentially arranged along the perimeter of the sensor body 102, such that the transducer 107 is disposed along a first perimeter portion of the sensor body 102, and the transducer 106 is disposed along a second perimeter portion of the sensor body, the first perimeter portion being different than the first.

The embodiment illustrated in FIG. 4 features many of the same elements and function as discussed above with respect to FIGS. 2 and 3. Here, however, a divider member 130 may be disposed between the transducers 106 and 107. The divider member 130 may be opaque to the wavelengths of light emitted by the transducers 106 and 107 and/or the light source 108, thereby isolating the measurement signals received from the respective transducers 106, 107. In embodiments in which an opaque divider member 130 is provided, signal produced by the first and second transducers 107, 106 may be naturally isolated. The first and second indicator molecules 105, 104 of the first and second transducers 107, 106, respectively, may emit light at the same wavelength or at different wavelengths.

Figure 5:
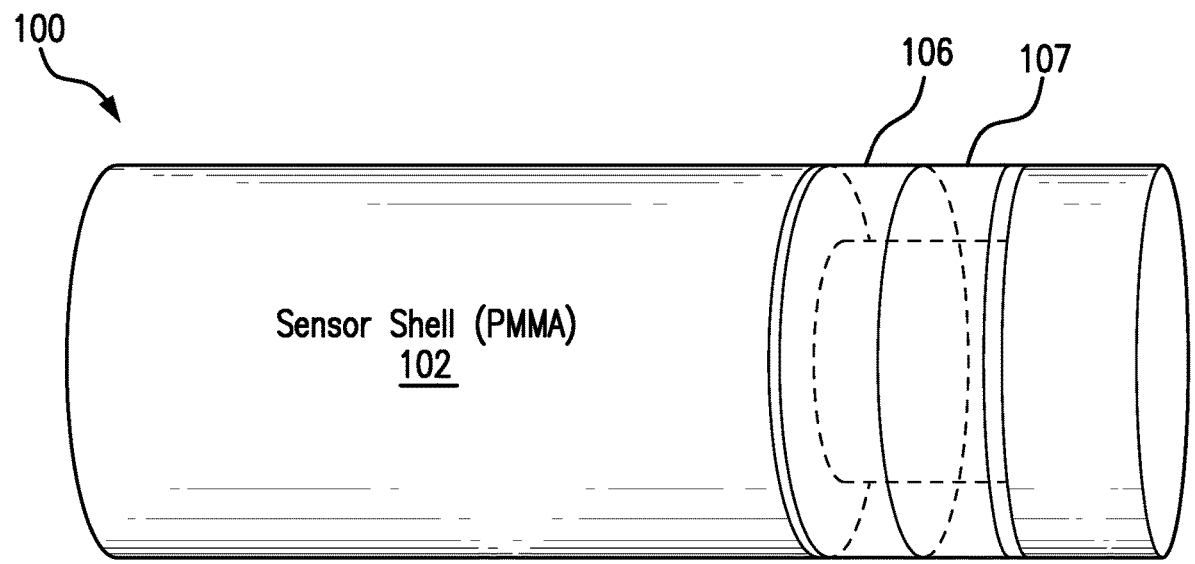
FIGS. 5 and 6 illustrate perspective views of a sensor embodying aspects of the present invention.
Figure 6:
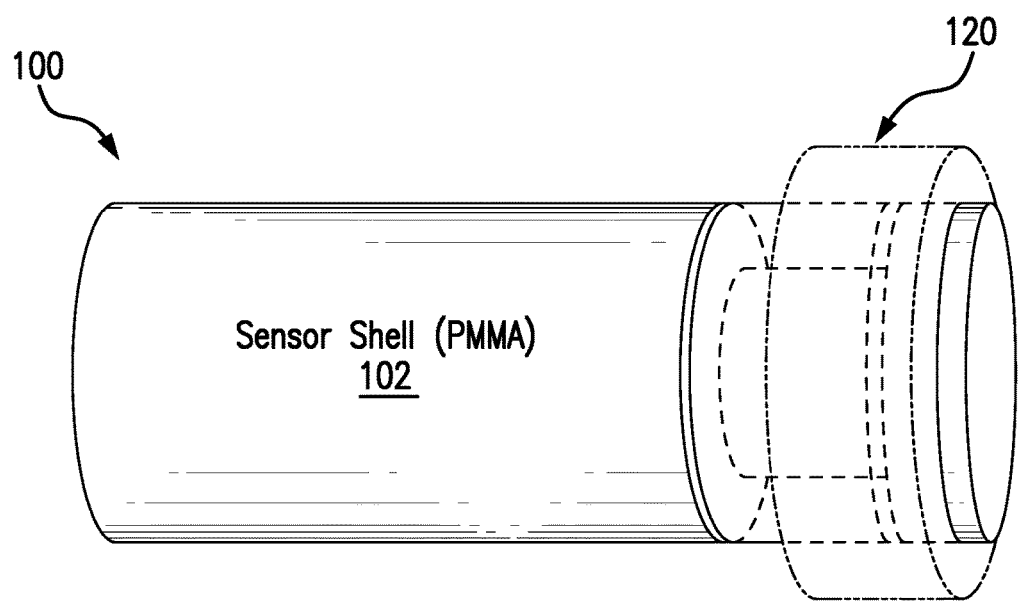

FIGS. 5-8 illustrate exemplary arrangements for providing a diffusion barrier over one or more of the first and second transducers 107, 106. FIG. 5 illustrates a sensor 100 without a diffusion barrier 120, and FIG. 6 shows the sensor 100 with the diffusion membrane 120. In some non-limiting embodiments, the sensor 100 may have a sensor housing/shell 102 and transducers 106, 107 embedded within and/or covering at least a portion of the housing 102. In some embodiments, the first transducer 107 may include one or more first indicator molecules 105, and the second transducer 106 may include one or more second indicator molecules 104, as discussed above.

In some embodiments, the diffusion barrier 120 may be a polymer membrane that is deposited over the surface of sensor body 102. The polymer membrane may then be partially or fully removed from a portion of the sensor body 102, such as directly over transducer 106 to thereby reduce the diffusion lag time associated with transducer 106. In other embodiments, the lag time may be selectively controlled by machining or processing the membrane after deposition on the sensor body. In still other embodiments, portions of the sensor body 102 may be wrapped in a removable material prior to applying the polymer membrane, thereby selectively preventing or inhibiting the membrane from being deposited over the transducer 106 and/or other portions of the sensor body 102.

Figure 7:
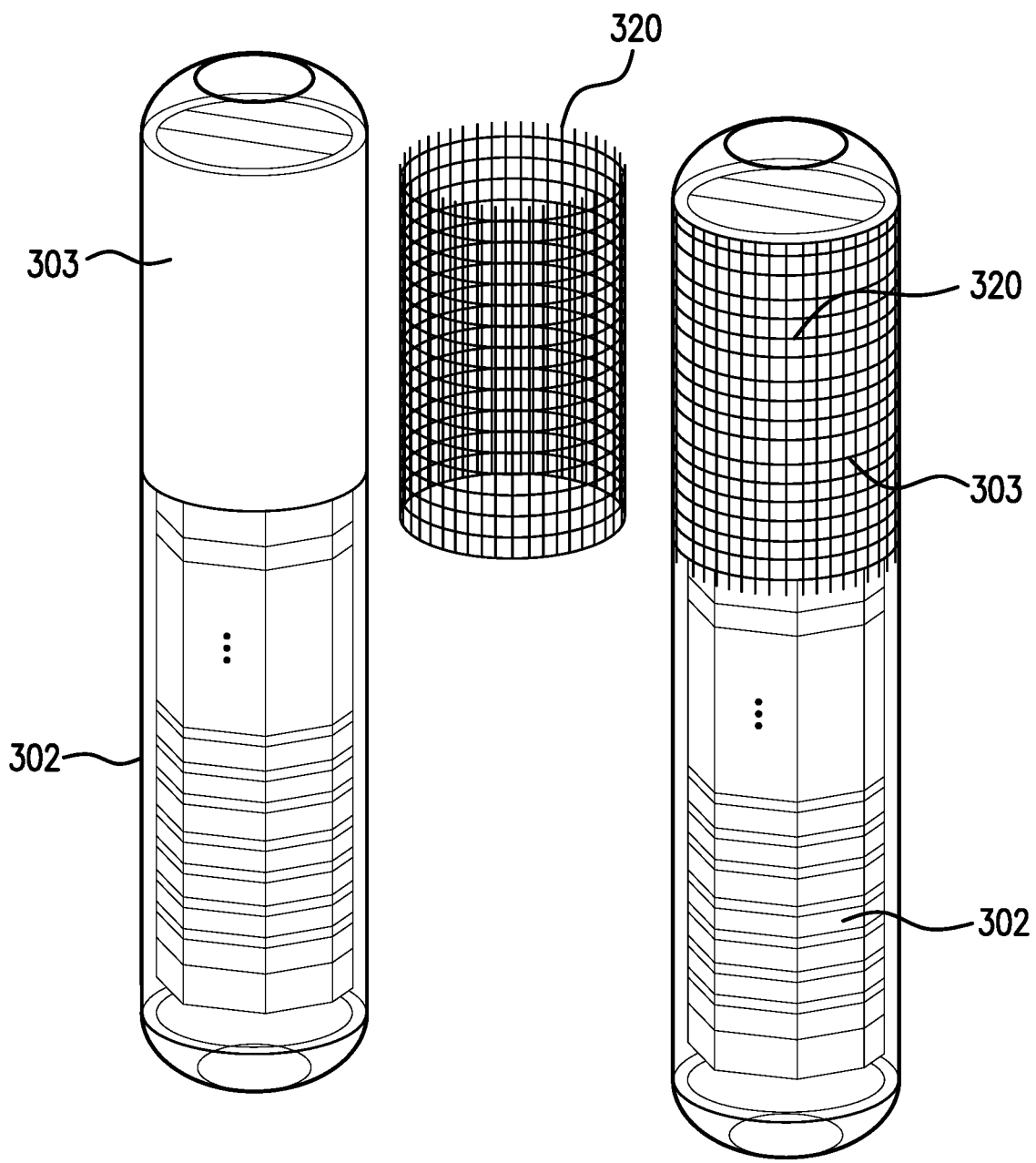
FIG. 7 illustrates perspective views of a sensor embodying aspects of the present invention.

As illustrated in the exemplary embodiment of FIG. 7, a mesh 320 may be provided over a portion 303 of the sensor body 302. One or more of the transducers may be disposed within the sensor body portion 303. The mesh 320 may itself act as a diffusion barrier. For example, mesh fibers (e.g., metallic or polymeric fibers) may be woven at selected densities in order to selectively control the diffusion characteristics at different positions along the mesh 320. In other embodiments, a graft material (e.g., a polymeric graft) may be affixed to the mesh 320, which may then be affixed at a selected portion of the sensor body 302 (see also FIG. 6, depicting a polymeric graft affixed to a selected portion of a sensor body).

Figure 8:
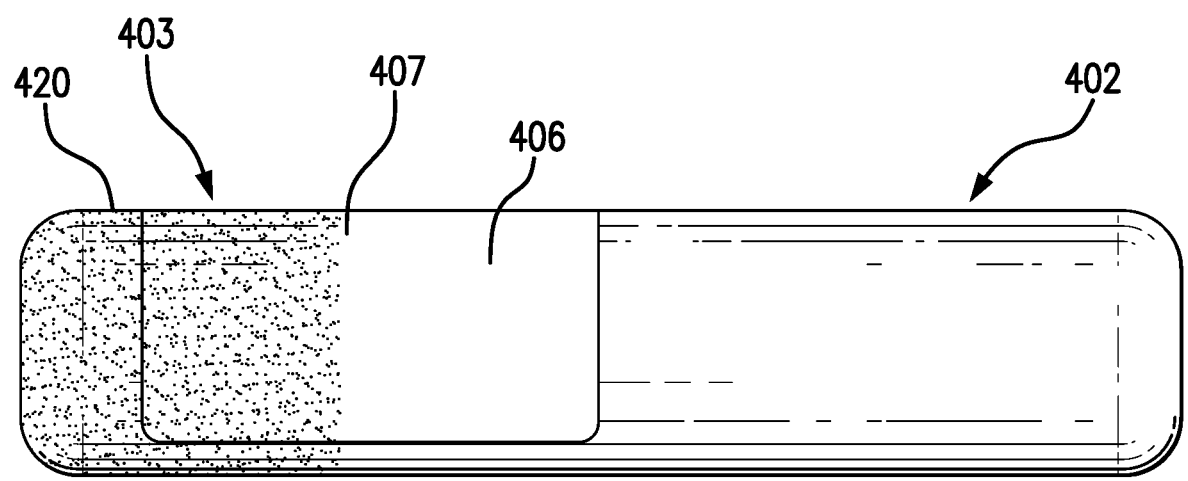
FIG. 8 illustrates a side view of a sensor embodying aspects of the present invention.

FIG. 8 illustrates an exemplary embodiment in which a material is selectively sputtered onto a portion 403 of a sensor body 402, thereby forming a diffusion barrier 420. As shown in FIG. 8, the diffusion barrier 420 may cover transducer 407 but not transducer 406. In other embodiments, the diffusion barrier 420 may cover both transducer 406 and 407, but may be deposited to form a thicker or denser coating over transducer 407 relative to transducer 406.

Figure 9:
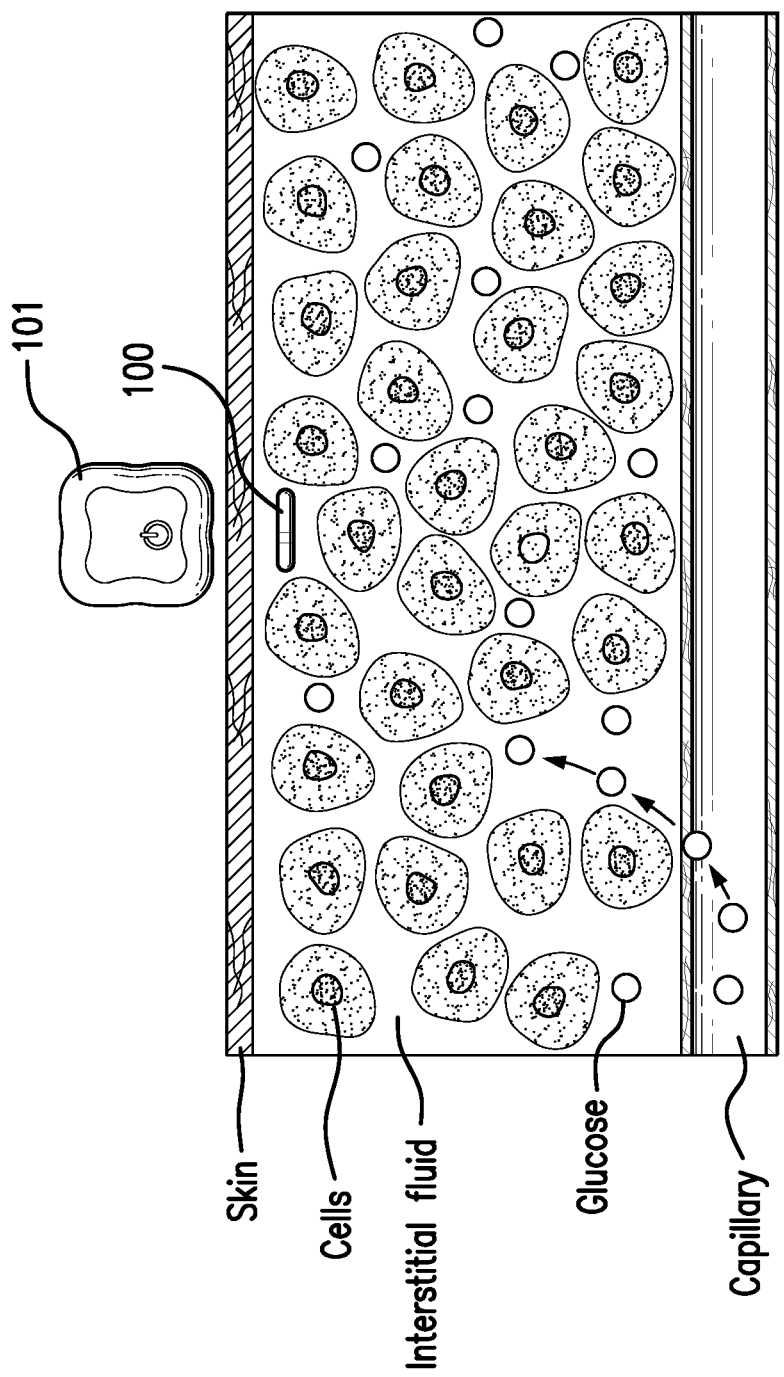
FIG. 9 illustrates a diagram of a sensor implanted subcutaneously according to embodiments of the present invention.

FIG. 9 depicts a diagram in which a sensor 100 is implanted within the interstitial fluid under a subject's skin and proximate to a capillary. In some embodiments, it may be desired to precisely estimate a concentration of analyte contained within the subject's blood. For example, the analyte monitoring system may be used to estimate a blood glucose level within a capillary as depicted in FIG. 9. Analyte molecules (e.g., glucose) may diffuse from the capillary through the interstitial fluid toward the sensor 100. After reaching the sensor 100, the analyte molecules may diffuse through any diffusion barriers and into the transducers to interact with indicator molecules disposed therein. The sensor 100 is able to detect analyte concentration when the analyte molecules reach and interact with the indicator molecules contained in the transducers.

In human subjects with diabetes, meanwhile, blood analyte concentration may change significantly over time, which in turn causes the interstitial fluid analyte concentration ($C_{ISF}$) to change over time. Due to the lag time required for analyte to diffuse from the capillary through the interstitial fluid to the sensor transducers, measurement accuracy can be improved by calculating the interstitial fluid rate of change ($R_{ISF}$), and using the measured $C_{ISF}$ in combination with the calculated $R_{ISF}$ to estimate the current blood analyte level. By using at least two transducers associated with different lag times as described above, it is possible to determine the $R_{ISF}$ with a single measurement (e.g., by performing a swipe measurement).

FIG. 11 is a flow chart illustrating an exemplary process 1100 for measuring an analyte concentration. In some embodiments, the process 1100 may include a step 1102 in which a transceiver 101 may detect that it is positioned within a proximity of a sensor 100. For example, the sensor may be subcutaneously implanted within an analyte-containing medium (e.g., interstitial fluid), and the transceiver 101 may be swiped, waved, or held within the sensor proximity. The proximity detection may be performed according to the systems and processes discussed in U.S. patent application Ser. No. 13/650,016, which is incorporated by reference in its entirety.

In some embodiments, the process 1100 may include a step 1104 in which, in response to detecting that the transceiver is proximate the sensor, the transceiver 101 may transmit to the sensor power sufficient to perform at least a first measurement using a first transducer 107 of the sensor 100 and a second measurement using a second transducer 106 of the sensor 100. Power may be transmitted via inductive elements as described above with respect to FIGS. 1-3. The transceiver 101 may also transmit one or more commands to the sensor 100, the one or more commands instructing the sensor 100 to perform one or more measurements, such as the first and second measurements described above.

In some embodiments, the method 1100 may include a step 1106 in which the sensor 100 may perform a first measurement of a detectable property exhibited by a first transducer 107 and a second measurement of a detectable property exhibited by a second transducer 106. The first and second transducers 107, 106 may exhibit one or more detectable properties based on an amount or concentration of an analyte in proximity to the respective first and second transducers 107, 106. In some embodiments, the first measurement may be indicative of an amount or concentration of an analyte in proximity to the first transducer 107 after passing through a first diffusion barrier 120. In some embodiments, the second measurement may be indicative of an amount or concentration of an analyte in proximity to the second transducer 106 after passing through a second diffusion barrier 121 (if present). In some embodiments, one or more of the first measurement and second measurement may be performed using the power transmitted in step 1204.

In some embodiments (e.g., embodiments in which the sensor 100 has more than two transducers associated with different time lags (see FIG. 10)), the sensor 100 may perform one or more additional measurements of a detectable property of the one or more additional transducers. In some embodiments, the additional transducers (e.g., third and fourth transducers 1008 and 1009 of FIG. 10) may exhibit one or more detectable properties based on an amount or concentration of an analyte in proximity to the one or more additional transducers. In some embodiments, a third measurement may be indicative of an amount or concentration of an analyte in proximity to the third transducer 1008 after passing through a second diffusion barrier 121. In some embodiments, the fourth measurement may be indicative of an amount or concentration of an analyte in proximity to a fourth transducer 1009 after passing through a third diffusion barrier 122. In some embodiments, the third and/or fourth measurements may be performed using the power transmitted in step 1104.

In some embodiments, the method 1100 may include a step 1108 in which the sensor 100 may convey and the transceiver 101 may receive first sensor data corresponding to the first measurement and second sensor data corresponding to the second measurement. In some embodiments, the step 1108 may include the transceiver 101 receiving the first sensor data.

In some embodiments, the method 1100 may include a step 1110 in which the transceiver 101 (or other device) may calculate an interstitial fluid analyte level rate of change $R_{ISF}$ based on at least the first sensor data, the second sensor data, and a diffusion rate of the first diffusion barrier. In some embodiments, $R_{ISF}$ may be calculated further based on a diffusion rate of the second diffusion barrier 121. In embodiments with more than two diffusion barriers, these diffusion rates and additional sensor data may also be taken into account when calculating $R_{ISF}$ in step 1108.

In some embodiments where two transducers are used, $R_{ISF}$ may be calculated according to the following formula, in which $C_{G1}$ represents the analyte measurement from the first transducer 107, $C_{G0}$ represents the analyte measurement from the second transducer 106, $\tau_1$ represents the delay associated with the first diffusion barrier 120, and $\tau_0$ represents the delay associated with the second diffusion barrier 121, if present.

$$R_{ISF} \approx \frac{C_{G1}(t) - C_{G0}(t)}{\tau_1 - \tau_0}$$

In some embodiments, the method 1100 may include a step 1112 in which the transceiver 101 (or other device) may calculate a blood analyte level based on the interstitial fluid analyte level (as measured by the first and/or second transducers) and $R_{ISF}$ as calculated in step 1108. In some embodiments, blood analyte level $C_B$ may be calculated according to the following formula, in which $p_1$ represents the rate at which analyte in the interstitial fluid is consumed (e.g., by cells) and $p_2$ represents the rate at which glucose diffuses from the blood vessel to the interstitial fluid immediate proximate the sensor, and $C_{G0}$ represents the analyte measurement from the second transducer (which may be associated with a shorter lag time).

$$C_B(t) = \frac{1}{p_2} R_{ISF} + \left(1 + \frac{p_1}{p_2}\right) C_{G_0}(t)$$

In some embodiments, the method 1100 may include a step 1114 in which the transceiver 101 may be removed from the proximity of the sensor 100. The transceiver 101 may be removed from the proximity of the sensor 100 at any time after the first sensor data and second sensor data are received. Further, the transceiver 101 may be removed before additional measurements are performed. In this manner, the transceiver 101 may be positioned (e.g., swiped) proximate to the sensor 100 for a brief time sufficient to perform a single measurement cycle and removed from the proximity of the sensor 100 immediately thereafter.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

The invention claimed is:

1. A sensor configured for at least partial placement in an analyte-containing medium, the sensor comprising:
    a first transducer that exhibits one or more detectable properties based on an amount or concentration of the analyte in proximity to the first transducer;
    a first diffusion barrier arranged such that, when the sensor is placed in the medium, the analyte contained in the medium diffuses through the first diffusion barrier before reaching the first transducer, wherein the first diffusion barrier is configured such that the analyte contained in the medium diffuses through the first diffusion barrier at a first diffusion rate $r_1$; and
    a second transducer that exhibits one or more detectable properties based on the amount or concentration of the analyte in proximity to the second transducer, wherein no diffusion barrier is disposed over the second transducer such that, when the sensor is placed in the medium, the analyte contained in the medium need not diffuse through a diffusion barrier before reaching the second transducer;
    wherein, when the sensor is placed in the medium, the analyte contained in the medium reaches the second transducer before the analyte contained in the medium reaches the first transducer.

2. The sensor of claim 1, wherein the first diffusion barrier is disposed over the first transducer, and the first diffusion barrier is configured such that, when the sensor is placed in the medium, the first diffusion barrier at least partially inhibits diffusion of the analyte to the first transducer.

3. The sensor of claim 1, further comprising a third transducer that exhibits one or more detectable properties based on the amount or concentration of the analyte in proximity to the third transducer.

4. The sensor of claim 3, further comprising a second diffusion barrier arranged such that, when the sensor is placed in the medium, the analyte contained in the medium diffuses through the second diffusion barrier before reaching the third transducer, wherein the second diffusion barrier is configured such that the analyte contained in the medium diffuses through the second diffusion barrier at a second diffusion rate $r_2$, wherein $r_1$ is greater than $r_2$.

5. The sensor of claim 1, wherein the first transducer comprises a first polymer graft and first indicator molecules, and the second transducer comprises a second polymer graft and second indicator molecules.

6. An analyte monitoring system, the system comprising:
    a sensor configured for at least partial placement in an interstitial fluid, the sensor comprising:
        a first transducer that exhibits one or more detectable properties based on an amount or concentration of an analyte in proximity to the first transducer;
        a first diffusion barrier arranged such that, when the sensor is placed in the interstitial fluid, the analyte contained in the interstitial fluid diffuses through the first diffusion barrier before reaching the first transducer, wherein the first diffusion barrier is configured such that the analyte contained in the interstitial fluid diffuses through the first diffusion barrier at a first diffusion rate $r_1$; and
        a second transducer that exhibits one or more detectable properties based on the amount or concentration of the analyte in proximity to the second transducer, wherein no diffusion barrier is disposed over the second transducer such that, when the sensor is placed in the interstitial fluid, the analyte contained in the interstitial fluid need not diffuse through a diffusion barrier before reaching the second transducer; and
    a transceiver configured to:
        receive first sensor data collected from the first transducer;
        receive second sensor data collected from the second transducer;
        calculate an interstitial fluid analyte level rate of change based on at least the first sensor data, the second sensor data, and the first diffusion rate $r_1$.

7. The analyte monitoring system of claim 6, wherein the first transducer comprises a first polymer graft and first indicator molecules, and the second transducer comprises a second polymer graft and second indicator molecules.

8. A method for detecting the rate of change of an analyte concentration in a medium, the method comprising:
    using a first transducer of a sensor of an analyte monitoring system to exhibit one or more detectable properties based on an amount or concentration of an analyte in proximity to the first transducer, wherein a first diffusion barrier of the sensor is arranged such that, when the sensor is placed in the interstitial fluid, the analyte contained in the interstitial fluid diffuses through the first diffusion barrier before reaching the first transducer, and the first diffusion barrier is configured such that the analyte contained in the interstitial fluid diffuses through the first diffusion barrier at a first diffusion rate $r_1$;
    using a second transducer of the sensor to exhibit one or more detectable properties based on the amount or concentration of the analyte in proximity to the second transducer, wherein no diffusion barrier is disposed over the second transducer such that, when the sensor is placed in the interstitial fluid, the analyte contained in the interstitial fluid need not diffuse through a diffusion barrier before reaching the second transducer;
    using the sensor to perform a first measurement of the one or more detectable properties exhibited by the first transducer and a second measurement of the one or more detectable properties exhibited by the second transducer;

using a transceiver of the analyte monitoring system to receive from the sensor at least first sensor data corresponding to the first measurement and second sensor data corresponding to the second measurement;

using a processor of the transceiver to calculate an analyte level rate of change based on at least the first sensor data, the second sensor data, and a first diffusion rate $r_1$ of the analyte through the first diffusion barrier.

9. The method of claim 8, further comprising using the processor of the transceiver to calculate an interstitial fluid analyte level based on at least one of the first sensor data and the second sensor data; and using the processor of the transceiver to calculate a blood analyte level based on the interstitial fluid analyte level and the analyte level rate of change.

10. The method of claim 8, further comprising:

using the transceiver to detect that the transceiver is positioned within a proximity of the sensor;

using the transceiver to, in response to detecting that the transceiver is proximate the sensor, transmitting from the transceiver to the sensor power sufficient to perform the first measurement and the second measurement, the transmitted power being used to perform the first measurement and the second measurement;

after receiving from the sensor the first sensor data and the second sensor data, and before additional measurements are performed, removing the transceiver from the proximity of the sensor.

11. The method of claim 8, wherein the first transducer comprises a first polymer graft and first indicator molecules, and the second transducer comprises a second polymer graft and second indicator molecules.

* * * * *